US00PP09109P

United States Patent [19]

McRae

[11] Patent Number: Plant 9,109

[45] Date of Patent: Apr. 18, 1995

[54] ASIATIC LILY PLANT NAMED 'SNOW CRYSTAL'

[75] Inventor: Edward A. McRae, Sandy, Oreg.

[73] Assignee: Cebeco Lilies, Inc., Aurora, Oreg.

[21] Appl. No.: 225,829

[22] Filed: Apr. 11, 1994

[51] Int. Cl.[6] ..... A01H 5/00

[52] U.S. Cl. ..... Plt./87.4

[58] Field of Search ..... Plt. 87.4

*Primary Examiner*—James R. Feyrer

*Attorney, Agent, or Firm*—Klarquist Sparkman Campbell Leigh & Whinston

[57] ABSTRACT

A new and distinct dwarf Asiatic lily hybrid named 'Snow Crystal' characterized by numerous medium-sized white flowers of excellent form and persistence, with orange pollen and on short stems with abundant foliage for pot plant culture.

1 Drawing Sheet

BACKGROUND OF THE INVENTION

The present invention comprises a new and distinct cultivar of Lilium hybrid, referred to commercially as an upright Asiatic hybrid pot lily, hereinafter sometimes referred to by the cultivar name 'Snow Crystal'.

This invention was originated from a hybridization made by the inventor in a controlled breeding program in Aurora, Oreg. The seed and pollen parent plants are unnamed Asiatic lily hybrid seedlings. More specifically, this plant is a product of seed parent A-112-80 crossed with pollen parent A-077-82. These parent plants are proprietary, non-released plants. This plant was developed for pot plant production and short stature.

This invention is distinguished by its numerous medium-sized white flowers with bright orange pollen produced on short strong stems with abundant rich green foliage. It is unique in its pure unspotted, unblotched white flower color on a true dwarf stem. It has extremely uniform stem height regardless of bulb size. It was selected for its attractive creamy white buds and short stems requiring no growth regulators. Lilium 'Snow Crystal' does not need large bulbs for good flower number. This is a distinct advantage in a pot plant. This plant flowers annually mid-season, has a vigorous and upright growth habit, and bulbs of this plant may be precooled and forced out of season for pot plant production. In addition, this new lily is highly resistant to disease and shows high tolerance to virus.

Of the many cultivars known to the inventor, the inventor is not aware of any other genetically dwarf Asiatic pot lily exhibiting the unblotched white color of this new variety.

Asexual reproduction of this new variety has been accomplished by scaling and tissue culture at the above location. The resulting plants have demonstrated that the above-mentioned unique characteristics are firmly fixed and are retained through successive generations reproduced by asexual reproduction.

Figure 2:
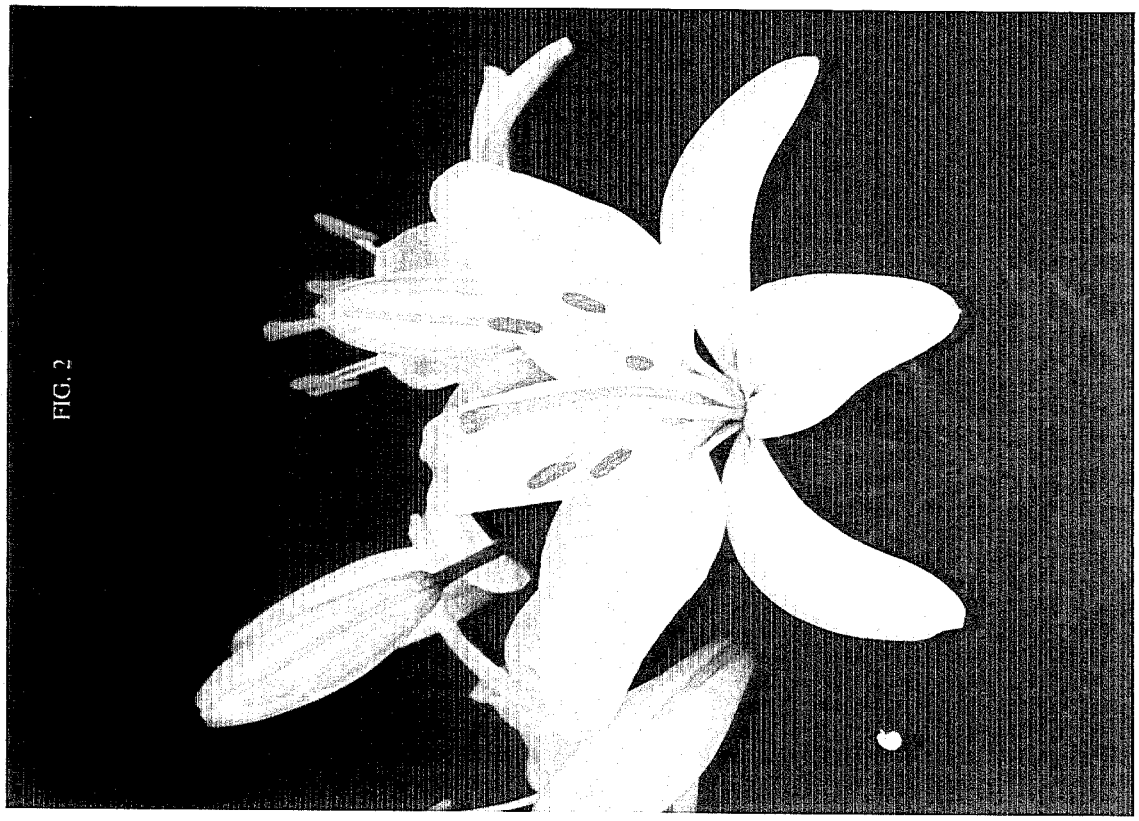
FIG. 2 is a close-up photograph which illustrates in greater detail a single flower of the new plant.
Figure 1:
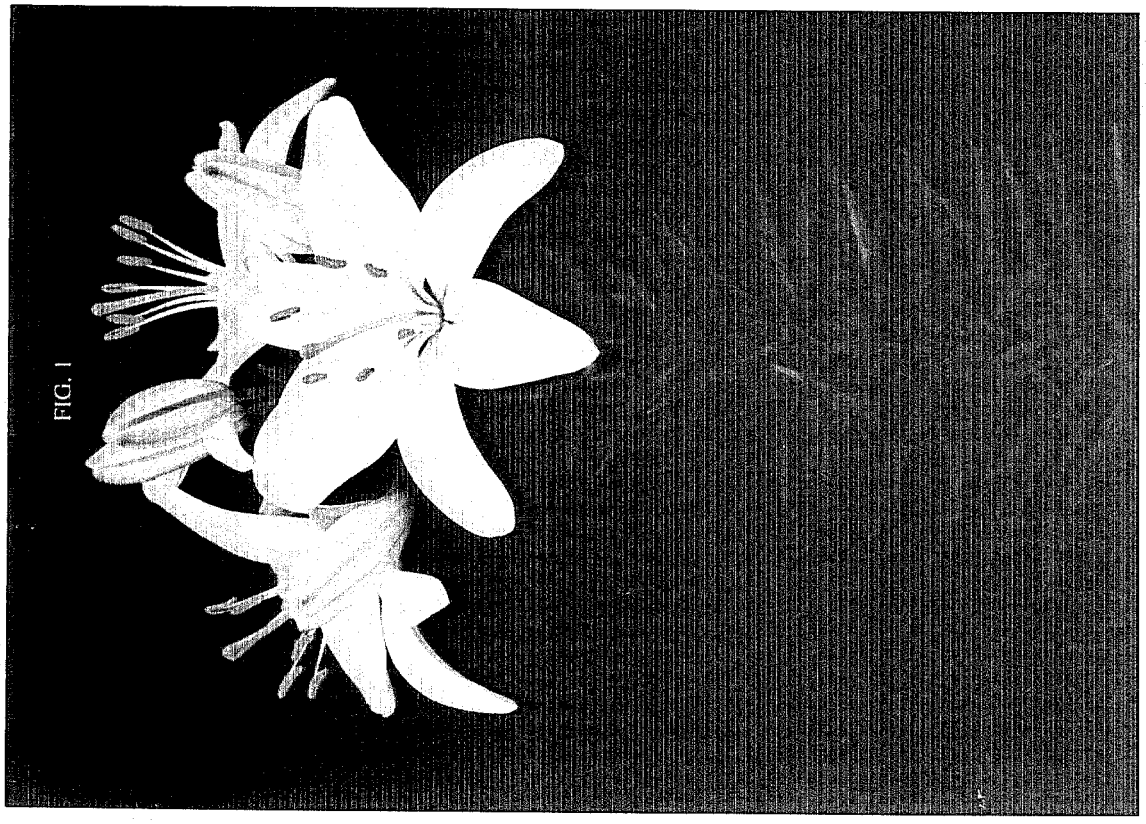
FIG. 1 is a photograph showing the 'Snow Crystal' lily.

The photographs of the drawing were taken in September 1993 in a studio and illustrate the typical flower and foliage form, with color being as true as is reasonably possible in this type of color photograph.

DETAILED DESCRIPTION

The 'Snow Crystal' lily has not been observed under all possible environmental conditions. The phenotype may vary significantly with variations in environment such as temperature, light intensity, and day length. The following observations, measurements and comparisons describe plants grown under field growing conditions in Hubbard, Oreg., in June 1992. Color references are made to the Royal Horticultural Society Colour Chart (RHS), except where the context indicates a term having its ordinary dictionary meaning.

THE PLANT

Origin: Seedling.

Parentage:

*Seed parent.*—Unnamed seedling.

*Pollen parent.*—Unnamed seedling.

Commercial classification: Hybrid Asiatic lily cultivar, pot type.

Classification: Division I-A, Upright Asiatic Hybrid Lily, according to the Horticultural Classification of Lilies by the Royal Horticultural Society of London.

Form: Single erect stem bearing terminal cluster of medium-sized flowers.

Height: Variable, average about 21.5 cm, from the top of the soil to the top of the flowers from bulbs of 10–12 cm in circumference and provided the light levels are adequate to avoid stretching.

Growth habit: Vigorous, upright and rigid.

Foliage:

*Arrangement.*—Spiral and close together on stem.

*Quantity.*—Abundant.

*Leaf size.*—Variable. To about 9 cm long and about 1.5 cm wide.

*Leaf shape.*—Linear to lanceolate.

*Texture.*—Leathery.

*Aspect.*—Glossy.

*Color.*—Medium green.

Bulbs:

*Size.*—Variable, would range from 10 cm to about 14 cm in circumference for commercial use.

*Color.*—White.

THE BUD

Size: To about 5.5–6 cm long and 2 cm wide just prior to opening.

Shape: Ovoid with obtuse tip.

Rate of opening: The mature bud opens slowly in response to light.

Color: Creamy white. Yellow Group 11D with a faint red purple blush.

THE FLOWER

Blooming habit: Annually, once and profusely, mid-season.

Days to bloom: Flowers approximately 70 days after spring greenhouse planting under typical commercial flower forcing conditions of 15° C. night time temperatures.

Inflorescence size: About 11.5 cm high and 21 cm wide when there are five flowers present from bulbs that are 10 cm in circumference.

Flower size: Medium.

*Diameter.*—About 11.5 cm.

*Depth.*—About 4.5 cm.

Borne: Usually 5 to 7 in an umbel or a modified raceme from bulbs 10–14 cm in circumference.

Shape: When the flower first opens it is cup-shaped. Later, the shape flattens out and the tepals reflex slightly at the tips.

Tepalage:

*Number.*—Six.

*Arrangement.*—Imbricated.

*Texture.*—Spongy.

*Aspect.*—Satiny.

*Size.*—Length: About 6.5 cm. Width: Inner tepals — about 3 cm. Outer tepals — about 2.2 cm. Depth of Imbrication: About 5 mm.

*Nectary.*—Yellow-green, about 1 cm long, pubescent, the channels together, the color directly above Orange-White Group 159A.

*Projections.*—None.

*Spots.*—Not present.

*Blush.*—Not present.

*Color.*—Topside: Yellow-White Group 158D to White Group 155D. Bottomside: Same with slight Greyed-Purple Group 187C, blush near bottom.

*Discoloration.*—Little or none.

*Fragrance.*—None.

*Lasting quality.*—Good.

Pedicle:

*Length.*—Usually about 4 cm (range from about 3.5 cm to about 7 cm).

*Color.*—Yellow-Green Group 144A, mottled with Greyed-Purple Group 183A.

*Orientation.*—Ascending upwardly from about 45° to 80° from the horizontal.

THE REPRODUCTIVE ORGANS

Stamens:

*Number.*—Six, typical of the genus Lilium.

*Anthers before dehiscence.*—Size: About 1.5 cm. Color: Greyed-Orange Group 171C.

*Filaments.*—Length: About 4.5 cm. Color: Yellow-White Group 158A to 158D at base. Sometimes blushed pink.

*Pollen.*—Color: Bright orange. Orange-Red Group 32A.

Pistil:

*Number.*—One.

*Style.*—Length: About 4 cm. Color: Yellow-Green Group 151A, blushed with Greyed-Purple Group 183A.

*Stigma.*—Color: Greyed-Purple Group 184A.

THE FRUIT

Fertility: The fruit is fertile. Shape: Ovoid. Color at maturity: Soft Brown.

I claim:

1. A new and distinct Asiatic lily substantially as herein shown and described.

* * * * *